United States Patent
Zhang et al.

(10) Patent No.: US 12,195,477 B2
(45) Date of Patent: Jan. 14, 2025

(54) DERIVATIVE OF BERBERINE, AND THE PREPARATION METHOD AND APPLICATION THEREOF

(71) Applicant: Harbin Medical University, Heilongjiang (CN)

(72) Inventors: Yong Zhang, Heilongjiang (CN); Baofeng Yang, Heilongjiang (CN); Xin Liu, Heilongjiang (CN); Weina Han, Heilongjiang (CN); Limin Zhao, Heilongjiang (CN)

(73) Assignee: Harbin Medical University, Harbin (CN)

( * ) Notice: Subject to any disclaimer, the term of this patent is extended or adjusted under 35 U.S.C. 154(b) by 0 days.

(21) Appl. No.: 18/086,397

(22) Filed: Dec. 21, 2022

(65) Prior Publication Data
US 2023/0192716 A1 Jun. 22, 2023

(30) Foreign Application Priority Data

Dec. 21, 2021 (CN) .......................... 202111573181.3

(51) Int. Cl.
*C07D 491/147* (2006.01)
(52) U.S. Cl.
CPC .................. *C07D 491/147* (2013.01)
(58) Field of Classification Search
CPC ................................................ C07D 491/147
See application file for complete search history.

(56) References Cited

FOREIGN PATENT DOCUMENTS

CN 106083842 * 6/2016

OTHER PUBLICATIONS

WIPO translation of CN 106083842, downloaded on Feb. 24, 2024, pp. 1-9.*

* cited by examiner

*Primary Examiner* — Susanna Moore

(57) ABSTRACT

The present disclosure is related to a derivative of berberine, and the preparation method and applications thereof. The present derivative of berberine has a significant anti-myocardial ischemic effect, and its preparation route is feasible and reasonable with lower cost, less toxic and harmful reagents used, no environmental contamination, and is suitable for large-scale production. The cardioprotective derivative of berberine developed in the present disclosure and the preparation method thereof effectively provide a basis for developing novel cardioprotective medicaments, have a great economic benefit in the future, and bring a broad social benefit, leading to promising application prospects.

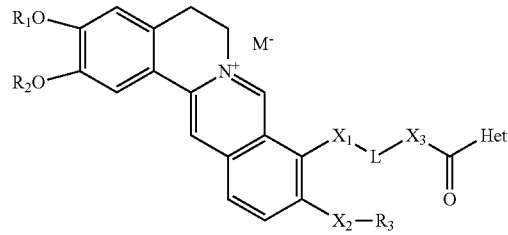

3 Claims, 10 Drawing Sheets

DERIVATIVE OF BERBERINE, AND THE PREPARATION METHOD AND APPLICATION THEREOF

CROSS-REFERENCE TO RELATED APPLICATION

This application claims priority from the Chinese patent application 202111573181.3 filed Dec. 21, 2021, the content of which is incorporated herein in the entirety by reference.

TECHNICAL FIELD

The present disclosure belongs to the field of pharmaceutical chemistry, and specifically, the present disclosure is related to a derivative of berberine and the preparation method thereof, and further to the use of the derivative of berberine.

BACKGROUND

With the aging population and the change of lifestyle in china, cardiovascular disease has become a major public health problem that threatens Chinese people's life and health. As noted in "Chinese Guideline on the Primary Prevention of Cardiovascular Disease (2020)", the mortality rate of ischemic heart disease relative to the overall mortality rate of cardiovascular diseases is increased from 40% in 1990 to 61% in 2016. Meanwhile, the annual average deaths increased from 1 million to 2.4 million during the same period, leading to an increasingly severe situation. Myocardial infarction (MI), i.e., ischemic myocardial necrosis, is caused by the decreased supply or enhanced demand for the coronary blood flow. MI is secondary to atherosclerosis of coronary artery, results in myocardial ischemia, and anoxia, and is commonly accompanied by arrhythmia, injured myocardial cells, cicatrization of cardiac tissue, cardiac remodeling, and cardiac dysfunction, finally leading to heart failure. The life health of human beings is severely threatened.

At present, the pharmaceuticals commonly used for myocardial ischemia clinically include antiplatelet agents, nitrates, β-receptor blocking agents and angiotensin converting enzyme inhibitory agents etc. However, the therapeutic effectiveness of these existing pharmaceuticals is still unsatisfactory in terms of life extension and mortality rate reduction, and most pharmaceuticals have some side effects. Accordingly, it is of great significance to develop potent and safe pharmaceuticals for anti-myocardial ischemia.

Berberine (5,6-dihydro-9,10-dimethoxybenzo[g]-1,3-benzodioxolane [5,6-α] quinolizine) belongs to the quaternary ammonium-type isoquinoline alkaloids. Berberine is a potent monomer mainly existing in plants from Berberidaceae, Papaveraceae, Ranunculaceae, Rutaceae, and Menispermaceae etc. Berberine possesses a series of pharmaceutical activities, including antidysenteric, anti-infectious protozoa, anti-tumor, hypoglycemic, blood lipid-lowering, antihypertensive and antiarrhythic activity etc. At present, berberine has been applied clinically due to its effects such as heat-clearing and detoxicating, and anti-microorganism. However, the low bioavailability of berberine limits its further applications. In the present disclosure, a derivative of berberine with novel structure has been obtained by modification. It has been found that the derivative has cardioprotective effect via anti-myocardial ischemia, based on which the present disclosure is proposed.

SUMMARY

The objective of the present disclosure is to provide a derivative of berberine with cardioprotective effect, and the preparation method and the cardioprotective use thereof. The synthetic route of the present derivative of berberine is simple, which may effectively save time and reduce cost for the synthesis. The present synthesis is simple to conduct, easy to implement, and suitable for industrial production. The compound provided by the present disclosure has significant cardioprotective effect, such as anti-myocardial ischemia effect, and several advantages, such as excellent safety, easy administration, cheap, and convenient transportation and storage etc.

Accordingly, the first aspect of the present disclosure provides the following technical scheme:

The present disclosure provides a derivative of berberine of Formula I, or the pharmaceutically acceptable salts, stereoisomers, polymorphisms, solvates and hydrates thereof:

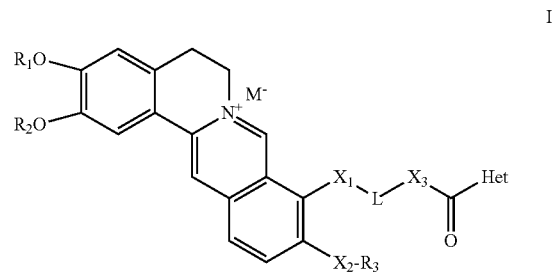

wherein,
$X_1$, $X_2$, and $X_3$ are independently selected from the group consisting of —O—, and —NH—;
$R_1$ and $R_2$ are independently selected from the group consisting of hydrogen, and —$C_{1-6}$ alkyl, or $R_1$ and $R_2$ form together —$CH_2$—, and —$CH_2CH_2$—;
$R_3$ is selected from the group consisting of hydrogen, —$C_{1-6}$ alkyl, —$C_{3-10}$ cycloalkyl, —COR, —COOR, —CONRR', —S(O)$_n$R, —P(O)(OR$^4$)$_2$, —$C_{6-14}$ aryl, -(5-14) member heteroaryl, —$C_{1-2}$ alkyl-$C_{6-10}$ aryl, and —$C_{1-2}$ alkyl-(5-14) member heteroaryl;
R and R' are independently selected from the group consisting of hydrogen, —$C_{1-6}$ alkyl, —$C_{3-10}$ cycloalkyl, —$C_{6-14}$ aryl, -(5-14) member heteroaryl, -(5-10) member heterocyclyl, —$C_{1-2}$ alkyl-$C_{6-10}$ aryl, and —$C_{1-2}$ alkyl-(5-14) member heteroaryl;
$R_4$ is selected from the group consisting of hydrogen, —$C_{1-6}$ alkyl, —$C_{6-10}$ aryl, —$C_{1-2}$ alkyl-$C_{6-10}$ aryl, ammonium group, and metal ions;
L is selected from the group consisting of $C_{1-10}$ alkylene;
Het is selected from the group consisting of -(5-14) member heteroaryl;
n is selected from 1 or 2;
M$^-$ represents an anion;
the above alkyl, cycloalkyl, aryl, heteroaryl, and heterocyclyl, either alone or as a part of any groups, are optionally substituted by one or more of the substituents selected from the group consisting of halogen, hydroxy, cyano, nitro, amino, —$C_{1-4}$ alkyl, —$C_{1-4}$ haloalkyl, —O—$C_{1-4}$ alkyl, —O—$C_{1-4}$ haloalkyl, —NH—$C_{1-4}$ alkyl, —COO—$C_{1-4}$ alkyl or —CO—$C_{1-4}$ alkyl.

The second aspect of the present disclosure is to provide a pharmaceutical composition comprising the derivative of berberine of Formula I, or the pharmaceutically acceptable salts, stereoisomers, polymorphisms, solvates and hydrates thereof.

The third aspect of the present disclosure is to provide a pharmaceutical composition comprising the derivative of berberine of Formula I or the pharmaceutically acceptable salts, stereoisomers, polymorphisms, solvates and hydrates thereof, and other medicaments useful for cardioprotection, anti-myocardial ischemia, and the treatment of myocardial infarction.

The fourth aspect of the present disclosure is to provide the use of the derivative of berberine of Formula I, or the pharmaceutically acceptable salts, stereoisomers, polymorphisms, solvates and hydrates thereof in manufacture of medications.

The fifth aspect of the present disclosure is to provide the preparation method of the derivative of berberine of Formula I.

Beneficial Effects:

With respect to the prior art, the beneficial technical effects of the present disclosure include:

1. A cardioprotective derivative of berberine and the preparation method thereof have been developed in the present disclosure, which effectively provide a basis for developing novel cardioprotective medicaments, have a great economic benefit in the future, and bring a broad social benefit, leading to promising application prospects.

2. The preparation route provided in the present disclosure is feasible and reasonable with lower cost, less toxic and harmful reagents used, and no environmental contamination. The overall yield of the resultant derivative of berberine is up to 71%, with an average purity of 98% or above, so that it is suitable for large-scale production.

3. The derivative of berberine of the present disclosure has a significant anti-myocardial ischemic effect: they can significantly improve the cardiac dysfunction of an ischemic heart, representing as increased ejection fraction (EF) and fraction shortening (FS) of the ischemic heart. In addition, said medication has enhanced the activities of superoxide dismutase (SOD) and adenosine triphosphate (ATP) in the cardiac cells injured by $H_2O_2$ in vitro. The derivatives can be used as a safe and potent medication for the prevention and treatment of myocardial ischemia:

(1) Significantly higher anti-myocardial ischemia effect over berberine: the derivatives of berberine of the present disclosure have obvious protective effect on the ischemic heart, have increased ejection fraction (EF) and fraction shortening (FS) of the ischemic heart, and have induced higher activities of superoxide dismutase (SOD) and adenosine triphosphate (ATP) in the cardiac cells injured by $H_2O_2$ in vitro as compared to berberine at the same dosage;

(2) Excellent safety: the derivatives of berberine of the present disclosure have higher tolerance dose with no obvious toxic and side effects;

(3) Simple and convenient administration, which can be easily adsorbed by human or animals via oral administration;

(4) The starting material of the medication provided in the present disclosure is berberine, enabling high drugability for the finished product. As compared with other imported medicaments for anti-myocardial ischemia, the medication provided herein is cheap, cost effective and can be easily accepted by patients;

(5) Convenient transportation and storage, which is only demanded for storage under cool and dry conditions with sealing.

DETAILED DESCRIPTION

Figure 1:
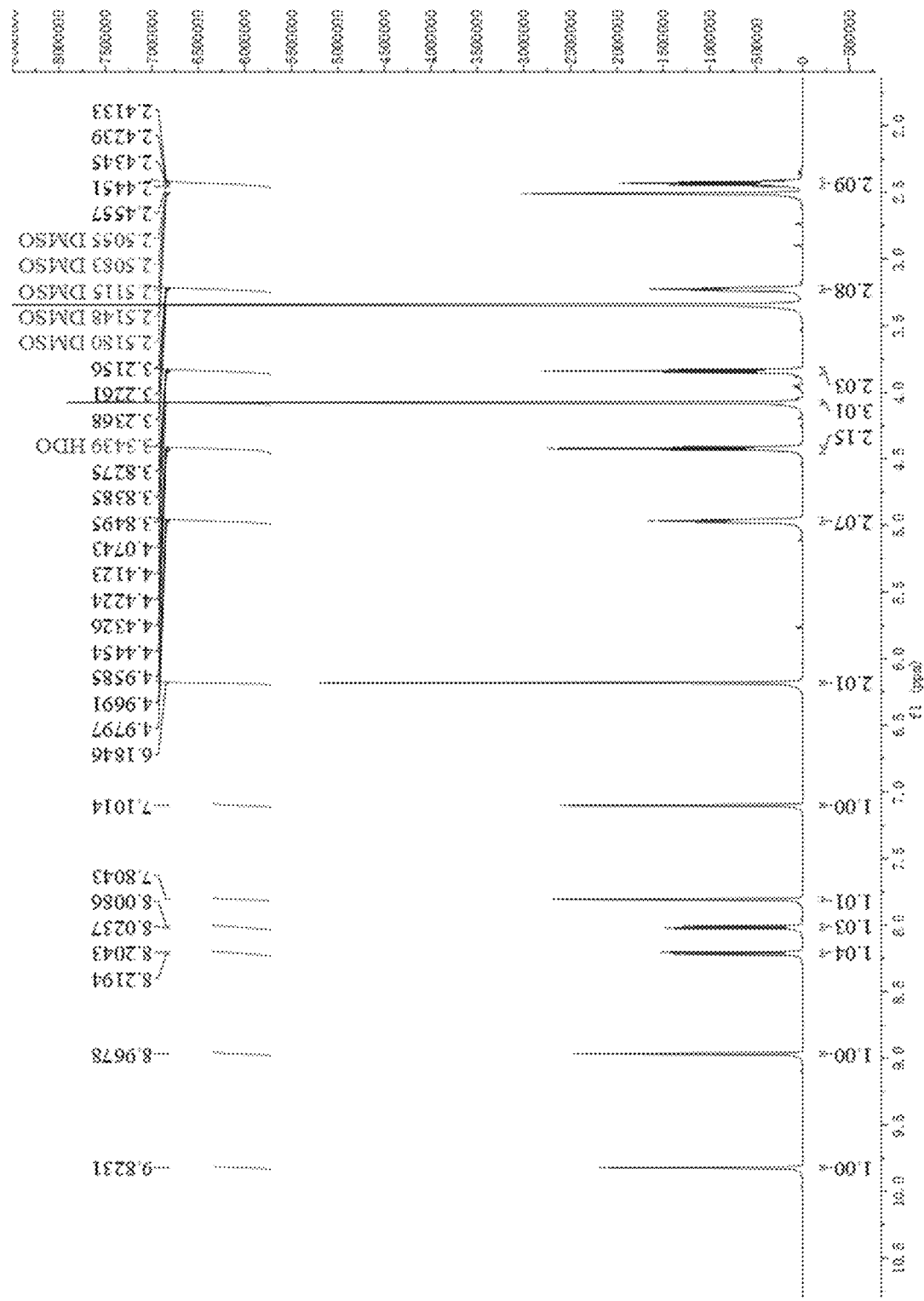
FIG. 1 illustrates the $^1H$ NMR spectrum of the intermediate brominated 9-O-bromopropyl berberine.

As used herein, the term "treatment", and other synonyms include the remission, alleviation or amelioration of the symptoms of the disease or disorder, the prevention of other symptoms, the amelioration and prevention of the potential metabolic causes for the symptoms, suppression of the disease or disorder, for example, arresting the development of the disease or disorder, remission of the disease or disorder, reversion of the disease or disorder, remission of the symptoms caused by the disease or disorder, or arrestment of the symptoms of the disease or disorder. In addition, the term encompasses the prophylactic purpose. The term further comprises obtaining therapeutic and/or prophylactic effect. The therapeutic effect refers to the cure or amelioration of the potential disease treated. Besides, the therapeutic effect also includes the cure or amelioration of one or more of the physiological symptoms related to potential diseases. For example, although the patient is still influenced by the potential disease, the amelioration has been observed. The composition can be administrated to the patients at a risk of suffering from specific diseases for the purpose of prophylaxis, or it can be administrated to the patients demonstrating one or more of the physiologic symptoms of the disease, even when no diagnosis of the disease has been made.

As used herein, the term "effective amount" refers to the amount of at lease one medicament or compound that is to some extent sufficient to alleviate one or more of the symptoms of the disease or disorder treated after administration. The consequences can include the reduction and/or remission of the evidences, symptoms or causes, or any other changes demanded by the biological system. For example, the "effective amount" for treatment is the amount of the composition comprising the compound disclosed herein that provides clinically significant remission of the disorders. Techniques, such as dose escalation test, can be used to determine the effective amount suitable for any individual case.

As used herein, the term "acceptable" refers to no long-term harmful effect on the general health of the subject treated.

As used herein, the term "pharmaceutically acceptable" refers to the substances, which have no influence on the biological activities or properties of the compound of the application (such as the carrier or adjuvant), and are relatively non-toxic, that is, the substances can be administrated to an individual with no unfavorable biologic response or interaction with any component contained in the composition in an unfavorable mode.

As used herein, the term "halogen" refers to fluorine, chlorine, bromine, or iodine.

As used herein, the term "alkyl" refers to the straight or branched saturated hydrocarbyl containing preferably 1-10 carbon atoms, preferably 1-6 carbon atoms, and more preferably 1-4 carbon atoms. The example of alkyl includes methyl, ethyl, n-propyl, isopropyl, n-butyl, isobutyl, t-butyl, pentyl or hexyl, etc.

As used herein, the term "cycloalkyl" refers to the saturated cyclic hydrocarbyl containing preferably 3-12 carbon atoms, preferably 3-10 carbon atoms, and more preferably 3-8 carbon atoms. The example of cycloalkyl includes cyclopropyl, cyclobutyl, cyclopentyl, cyclohexyl, or cycloheptyl, etc.

As used herein, the terms "aryl" refers to the carbocyclic aryl containing preferably 6-18 carbon atoms, preferably 6-14 carbon atoms, and more preferably 6-10 carbon atoms. The aryl can be monocyclic, bicyclic or tricyclic. The example of aryl includes phenyl, naphthyl or anthryl, etc.

As used herein, the terms "heteroaryl" refers to the heterocyclic aryl containing preferably 5-14 cyclic atoms, and at least one heteroatom selected from O, N, and S, and optionally containing 1-3 additional heteroatoms independently selected from O, N, and S. The number of cyclic atoms on the heteroaryl is preferably 5-10, and more preferably 5-6. The linkage sites between the heteroaryl and other groups can be located at any heteroatom or carbon atom on the cycle, so as to form a stable structure. The example of heteroaryl includes pyrrolyl, thienyl, furyl, oxazolyl, thiazolyl, imidazolyl, pyrazolyl, isoxazolyl, isothiazolyl, triazolyl, oxadiazolyl, thiadiazolyl, pyridyl, pyrimidinyl, pyridazinyl, pyrazinyl, pyranyl, indyl, isoindolinyl, indazolyl, benzofuranyl, benzothiophenyl, benzimidazolyl, benzothiazolyl, purinyl, quinolyl, isoquinolyl, quinolizinyl, quinazolinyl, quinoxalyl, naphthyridinyl, or pteridyl, etc.

As used herein, the terms "heterocyclyl" refers to the saturated or partially unsaturated heterocyclyl containing preferably 5-14 cyclic atoms, and at least one heteroatom selected from O, N, and S, and optionally containing 1-3 additional heteroatoms independently selected from O, N, and S. The number of cyclic atoms on the heterocyclyl is preferably 5-10, and more preferably 5-7. The linkage sites between the heterocyclyl and other groups can be located at any heteroatom or carbon atom on the cycle, so as to form a stable structure. The example of heterocyclyl includes pyrrolidinyl, pyrrolinyl, imidazolidinyl, imidazolinyl, pyrazolidyl, pyrazolinyl, tetrahydrofuranyl, dioxolanyl, piperidyl, piperazinyl, dioxanyl, morpholinyl, sulfomorpholinyl, dithianyl, trithianyl, high piperazinyl, or high piperazinyl, etc.

The first aspect of the present disclosure provides a derivative of berberine of Formula I, or the pharmaceutically acceptable salts, stereoisomers, polymorphisms, solvates and hydrates thereof:

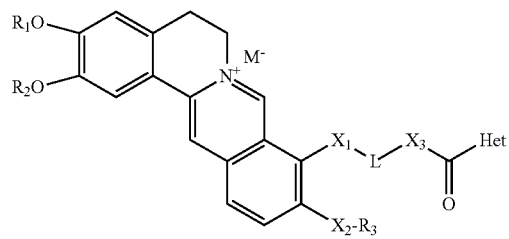

wherein, $X_1$, $X_2$, and $X_3$ are independently selected from the group consisting of —O—, and —NH—;

$R_1$ and $R_2$ are independently selected from the group consisting of hydrogen, and —$C_{1-6}$ alkyl, or $R_1$ and $R_2$ form together —$CH_2$—, —$CH_2CH_2$—;

$R_3$ is selected from the group consisting of hydrogen, —$C_{1-6}$ alkyl, —$C_{3-10}$ cycloalkyl, —COR, —COOR, —CONRR', —S(O)$_n$R, —P(O)(OR$^4$)$_2$, —$C_{6-14}$ aryl, -(5-14) member heteroaryl, —$C_{1-2}$ alkyl-$C_{6-10}$ aryl, and —$C_{1-2}$ alkyl-(5-14) member heteroaryl;

R and R' are independently selected from the group consisting of hydrogen, —$C_{1-6}$ alkyl, —$C_{3-10}$ cycloalkyl, —$C_{6-14}$ aryl, -(5-14) member heteroaryl, -(5-10) member heterocyclyl, —$C_{1-2}$ alkyl-$C_{6-10}$ aryl, and —$C_{1-2}$ alkyl-(5-14) member heteroaryl;

$R_4$ is selected from the group consisting of hydrogen, —$C_{1-6}$ alkyl, —$C_{6-10}$ aryl, —$C_{1-2}$ alkyl-$C_{6-10}$ aryl, ammonium group, and metal ions;

L is selected from the group consisting of $C_{1-10}$ alkylene;

Het is selected from the group consisting of -(5-14) member heteroaryl;

n is selected from 1 or 2;

$M^-$ represents an anion;

the above alkyl, cycloalkyl, aryl, heteroaryl, and heterocyclyl, either alone or as a part of any groups, are optionally substituted by one or more of the substituents selected from the group consisting of halogen, hydroxy, cyano, nitro, amino, —$C_{1-4}$ alkyl, —$C_{1-4}$ haloalkyl, —O—$C_{1-4}$ alkyl, —O—$C_{1-4}$ haloalkyl, —NH—$C_{1-4}$ alkyl, —COO—$C_{1-4}$ alkyl or —CO—$C_{1-4}$ alkyl.

In a preferable embodiment, $X_1$ is selected from —O—.
In a preferable embodiment, $X_2$ is selected from —O—.
In a preferable embodiment, $X_3$ is selected from —O—.
In a preferable embodiment, $R_1$ and $R_2$ are independently selected from the group consisting of hydrogen, and —$C_{1-4}$ alkyl.

In a preferable embodiment, $R_1$ and $R_2$ form together —$CH_2$—, and —$CH_2CH_2$—.

In a preferable embodiment, $R_3$ is selected from the group consisting of —$C_{1-4}$ alkyl, —$C_{3-7}$ cycloalkyl, —$C_{6-10}$ aryl, -(5-6) member heteroaryl, —$C_{1-2}$ alkyl $C_{6-10}$ aryl, and —$C_{1-2}$ alkyl-(5-6) member heteroaryl, and the above alkyl, cycloalkyl, aryl, heteroaryl, either alone or as a part of any groups, are optionally substituted by one or more of the substituents selected from the group consisting of halogen, hydroxy, cyano, nitro, amino, —$C_{1-4}$ alkyl, —$C_{1-4}$ haloalkyl, —O—$C_{1-4}$ alkyl, —O—$C_{1-4}$ haloalkyl, —NH—$C_{1-4}$ alkyl, —COO—$C_{1-4}$ alkyl or —CO—$C_{1-4}$ alkyl.

Preferably, $R_3$ is selected from the group consisting of methyl, ethyl, n-propyl, isopropyl, n-butyl, isobutyl, t-butyl, phenyl, naphthyl, benzyl, phenethyl, and pyridyl, and the above methyl, ethyl, n-propyl, isopropyl, n-butyl, isobutyl, t-butyl, phenyl, naphthyl, benzyl, phenethyl, and pyridyl are optionally substituted by one or more the substituents selected from the group consisting of halogen, hydroxy, cyano, nitro, amino, —$C_{1-4}$ alkyl, —$C_{1-4}$ haloalkyl, —O—$C_{1-4}$ alkyl, —O—$C_{1-4}$ haloalkyl, —NH—$C_{1-4}$ alkyl, —COO—$C_{1-4}$ alkyl or —CO—$C_{1-4}$ alkyl.

In a preferable embodiment, L is selected from —(CHR$_L$)$_m$—, wherein R$_L$ is selected from the group consisting of hydrogen, —$C_{1-4}$ alkyl, and m is selected from 1, 2, 3, 4, 5 or 6.

Preferably, L is selected from the group consisting of —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$—, —CH(CH$_3$)CH$_2$CH$_2$—, —C(CH$_3$)$_2$CH$_2$CH$_2$—, —CH$_2$CH(CH$_3$)CH$_2$—, and —CH$_2$C(CH$_3$)$_2$CH$_2$—.

In a preferable embodiment, Het is selected from the group consisting of -(5-10) member heteroaryl, which is optionally substituted by one or more of the substituents selected from the group consisting of halogen, hydroxy, cyano, nitro, amino, —$C_{1-4}$ alkyl, —$C_{1-4}$ haloalkyl, —O—$C_{1-4}$ alkyl, —O—$C_{1-4}$ haloalkyl, —NH—$C_{1-4}$ alkyl, —COO—$C_{1-4}$ alkyl or —CO—$C_{1-4}$ alkyl.

Preferably, Het is selected from the group consisting of -(5-6) member heteroaryl, which is optionally substituted by one or more of the substituents selected from the group consisting of halogen, hydroxy, cyano, nitro, amino, methyl, ethyl, n-propyl, isopropyl, n-butyl, isobutyl, sec-butyl, t-butyl, methoxyl, ethoxy, n-propoxy, isopropoxy, n-butoxy, t-butoxy, trifluoromethoxy, methylamino, ethylamino, —COOMe, —COOEt, —COMe, and —COEt.

Preferably, Het is selected from the group consisting of pyrrolyl, thienyl, furyl, oxazolyl, thiazyl, imidazolyl, pyrazolyl, isoxazolyl, isothiazolyl, triazolyl, oxadiazolyl, thiadiazolyl, pyridyl, pyrimidinyl, pyridazinyl, pyrazinyl, pyranyl, indyl, isoindolinyl, indazolyl, benzofuranyl, benzothiophenyl, benzimidazolyl, benzothiazolyl, purinyl, quinolyl, isoquinolyl, quinolizinyl, quinazolinyl, and quinoxalyl, which is optionally substituted by one or more of the substituents selected from the group consisting of halogen, hydroxy, cyano, nitro, amino, methyl, ethyl, n-propyl, isopropyl, n-butyl, isobutyl, sec-butyl, t-butyl, methoxyl, ethoxy, n-propoxy, isopropoxy, n-butoxy, t-butoxy, trifluoromethoxy, methylamino, ethylamino, —COOMe, —COOEt, —COMe, and —COEt.

In a preferable embodiment, M$^-$ is selected from the group consisting of F$^-$, Cl$^-$, Br$^-$, I$^-$, and CH$_3$COO$^-$.

In a preferable embodiment, the derivative of berberine of Formula I is selected from the group consisting of:

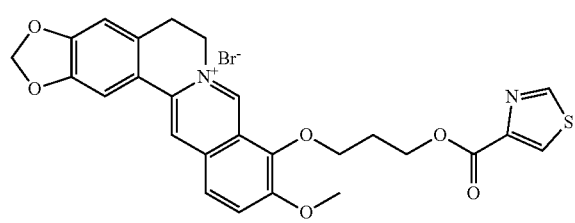

1

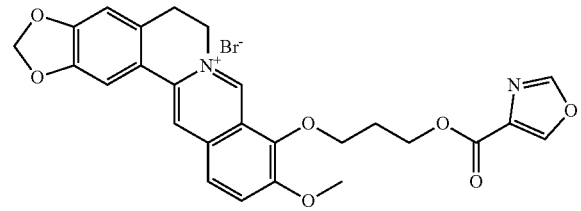

2

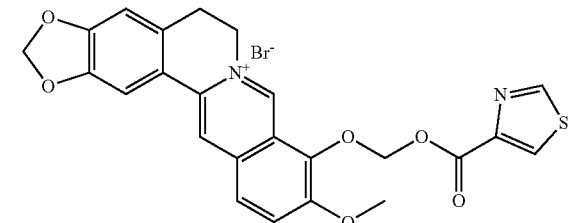

3

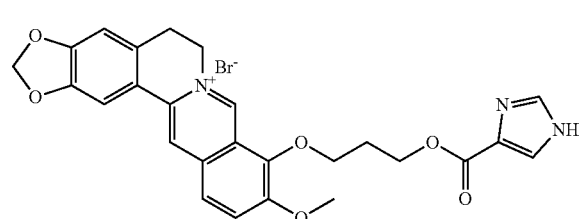

4

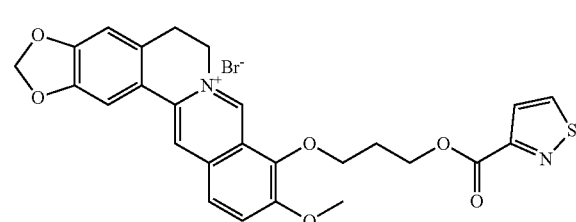

5

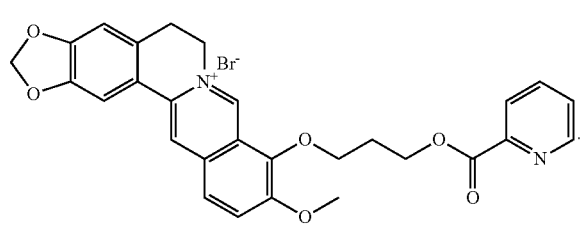

Preferably, the derivative of berberine of Formula I is selected from the group consisting of:

1

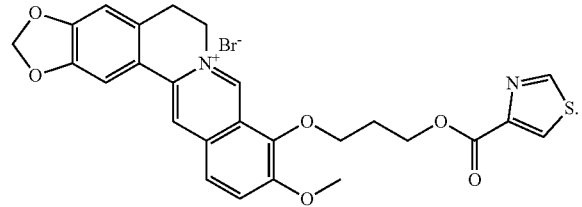 [SMILES: COc1ccc2cc3[n+](cc2c1OCCCOC(=O)c1cscn1)CCc1cc2c(cc1-3)OCO2 ; [Br-]]

The compound is represented by the molecular formula $C_{26}H_{23}BrN_2O_6S$ with a molecular weight of 571.44, and is named as: 9-(3-((thiazole-4-carbonyl)oxy)propoxy)-10-methoxy-5,6-dihydro-[1,3]dioxolo[4,5-g]isoquinolino[3,2-a]isoquinolin-7-ium bromide (bominated 9-O-propyl berberine thiazole formate).

In a preferable embodiment, the present derivative of berberine of Formula I comprises the stereoisomers thereof. When the compounds according to the present disclosure have at least 1 chiral center, they can be correspondingly present in the form of enantiomers. When the compounds have 2 or more chiral centers, they can be correspondingly present in the form of diastereoisomers. It is understood that all such isomers, and the mixtures thereof are comprised in the scope of the present disclosure.

In a preferable embodiment, the derivative of berberine of Formula I described herein includes the polymorphisms, solvates, and hydrates thereof.

In a preferable embodiment, the present derivative of berberine of Formula I includes the pharmaceutically acceptable salts thereof. For the application in pharmaceuticals, the salts of the present compounds are considered as non-toxic "pharmaceutically acceptable salts". However, other salts also can be used for preparing the compounds according to the present disclosure, or the pharmaceutically acceptable salts thereof. The pharmaceutically acceptable salts of the present compound include the acid addition salts formed by its free alkali compound with a common acid. The acids include inorganic and organic acids, such as: hydrochloric acid, hydrobromic acid, nitric acid, sulphuric acid, carbonic acid, ortho-phosphoric acid, trans-butenedioic acid, cis-butenedioic acid, propandioic acid, succinic acid, tartaric acid, formic acid, acetic acid, hexanoic acid, octanoic acid, capric acid, steric acid, 2,2-dichloroacetic acid, acylated amino acids, alginic acid, ascorbic acid, L-aspartic acid, benezenesulfonic acid, benzoic acid, 4-acetamidobenzoic acid, (+)-camphoric acid, camphorsulfonic acid, (+)-(1S)-camphor-10-sulfonic acid, cinnamic acid, citric acid, cyclohexane sulfamic acid, dodecylsulfuric acid, ethane-1,2-disulfonic acid, ethanesulfonic acid, 2-hydroxyethanesulfonic acid, galactaric acid, gentisic acid, glucoheptonic acid, D-gluconic acid, D-glucuronic acid, L-glutamic acid, α-oxo-glutaric acid, glycollic acid, hippuric acid, (+)-L-lactic acid, (±)-DL-lactic acid, lactobionic acid, (−)-L-malic acid, (±)-DL-mandelic acid, methane sulfonic acid, naphthalene-2-sulfonic acid, naphthalene-1,5-disulfonic acid, 1-hydroxy-2-naphthoic acid, nicotinic acid, oleic acid, orotic acid, oxalic acid, palmitinic acid, dihydroxynaphthalic acid, L-pyroglutamic acid, salicylic acid, 4-aminosalicylic acid, decanedioic acid, steric acid, p-toluenesulphonic acid, and undecylenic acid, etc.; representative pharmaceutically acceptable salts include: acetate, benzene sulfonate, benzoate, bicarbonate, bisulfate, bitartrate, bromide, camphorsulfonate, carbonate, citrate, hydrochloride, dihydrochloride, ethylsulfonate, gluceptate, gluconate, hydrobromide, lactate, lactobionate, malate, maleate, amygdalate, mesylate, naphthalene sulfonate, nitrate, oleate, palmitate, phosphate/diphosphate, salicylate, stearate, sulphate, succinate, tartrate, and tosylate etc.

Furthermore, when the compound of the present disclosure contains acidic moiety, the suitable pharmaceutically acceptable salts can include alkali metal salts, such as sodium or potassium salts; alkaline earth salts, such as calcium or magnesium salts; and the salts formed with suitable organic ligands, such as quaternary ammonium salts.

The second aspect of the present disclosure provides a pharmaceutical composition comprising the compound of Formula I of the present disclosure, or the pharmaceutically acceptable salts, pro-drugs, stereoisomers, crystals, solvates or hydrates thereof.

In a preferable embodiment, the pharmaceutical composition further comprises the pharmaceutically acceptable carriers, diluents or excipients. More preferably, the pharmaceutical composition is a compound preparation comprising the derivative of berberine of Formula I, or the pharmaceutically acceptable salts, stereoisomers, polymorphisms, solvates and hydrates thereof, and a pharmaceutically acceptable carrier, diluent or excipient.

Specific carrier, diluent or excipient used in the present disclosure depends on the application mode and purpose of the present compound. Suitable carrier, diluent or excipient includes: carbohydrates, water soluble or swollen polymers, hydrophilic or hydrophobic materials, waxes, gelatin, oils, solvents, water etc. Specifically, the above carrier, diluent or excipient can comprise, e.g., water, starch, lactose, dextrose, fructose, sucrose, polethylene glycol, propylene glycol, sorbitol, mannitol, polyvinyl alcohol, rubber, gelatin, alginate, calcium silicate, calcium phosphate, cellulose, syrup, methyl cellulose, polyvinyl pyrrolidone, alkyl parahydroxybenzosorbate, talc, magnesium stearate, steric acid, glycerol, sesame oil, sweet oil, and soybean oil, etc.

The pharmaceutical composition described in the present disclosure can further comprise one or more of binders, disintegrants, suspending aids, stabilizers, isotonic agents, surfactants, wetting agents, lubricants, buffering agents, solubility enhancers, emulsifiers, suspending agents, preservatives, antioxidants, opacifiers, flow aids, colorants, sweeteners, aromatics, flavouring agents, and other known additives.

The pharmaceutical composition of the present disclosure can be prepared by compounding the present derivative of berberine of Formula I, or the pharmaceutically acceptable salts, stereoisomers, solvates, polymorphisms thereof with suitable carriers, diluents, or excipients, and can be formulated in to the capsule, tablet, powder, granule, sustained release agent, injection or other formulations.

In a preferable embodiment, the pharmaceutical composition described in the present disclosure is a medication modified with a carrier. Preferably, the carrier can be selected from one or more of the advanced formulations, including microsphere, microemulsion, polymeric surfactant, nanoparticle, implant, etc. After modified by the carrier, the absorption and oral bioavailability of the active ingredients can be facilitated.

The pharmaceutical composition of the present disclosure may contain 0.01 to 99 wt % of the active ingredients, preferably, 0.01% to 50 wt %, preferably 0.1% to 10 wt %, more preferably 0.5% to 5 wt %, and most preferably 1% to 2 wt % of the active ingredients.

In the present disclosure, the dosage of the active ingredient can be varied in a wide range, for example, can be ranged from 1-1000 mg, preferably 10-500 mg, and more preferably 20-100 mg for adults. An effective amount of medication is provided at a dosage of generally about 0.1-50 mg/kg body weight, preferably 0.5-20 mg/kg, and more preferably 0.8-5 mg/kg body weight. The ideal dosage can be easily determined by a person of skill in the art, and varied based on the specific compound used, the administration route, the specification of the formulation, the administration route, and the progress of the disease. In addition, factors related to the specific patient treated, including the age, body weight, diet, and time for administration of the patient, may lead to the demand for a varied dosage. The pharmaceutical composition can be administrated by a single daily dosage.

Furthermore, the third aspect of the present disclosure provides a pharmaceutical composition comprising the derivative of berberine of Formula I, or the pharmaceutically acceptable salts, stereoisomers, polymorphisms, solvates and hydrates thereof, and other medicaments useful for cardioprotection, anti-myocardial ischemia, and the treatment of myocardial infarction.

Preferably, said other medicaments can be selected from one or more of the diuretics, vasodilators, nervous-endocrine system regulators.

In the present disclosure, a myocardial infarction model has been created for observing the cardioprotective effect of the derivative of berberine on the testing myocardial infarct mice. It has been found that the derivative of berberine is able to significantly improve the cardiac functions of an ischemic heart, representing as increased ejection fraction (EF), and fraction shortening (FS) of the ischemic heart. Meanwhile, it has been demonstrated by in vitro experiments that the present derivative of berberine is able to enhance the activity of superoxide dismutase (SOD) in the cardiac cells injured by $H_2O_2$ in vitro, and is also able to improve the generation of adenosine triphosphate (ATP) in the cardiac cells injured by $H_2O_2$ in vitro. Thus, the derivative of berberine of the present disclosure has the following effects, including cardioprotection, anti-myocardial ischemia, and the treatment of myocardial infarction.

Accordingly, the fourth aspect of the present disclosure provides the use of the derivative of berberine of Formula I, or the pharmaceutically acceptable salts, polymorphisms, solvates, and hydrates thereof in cardioprotection, anti-myocardial ischemia, and the treatment of myocardial infarction.

Similarly, the present disclosure provides the use of the derivative of berberine of Formula I, or the pharmaceutically acceptable salts, stereoisomers, polymorphisms, solvates and hydrates thereof in manufacture of medicaments for cardioprotection, anti-myocardial ischemia, or the treatment of myocardial infarction.

The fifth aspect of the present disclosure also provides the preparation method of the present derivative of berberine of Formula I, which comprises the following steps:

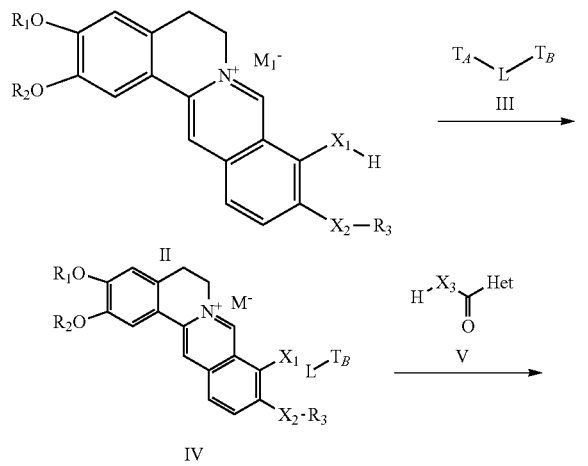

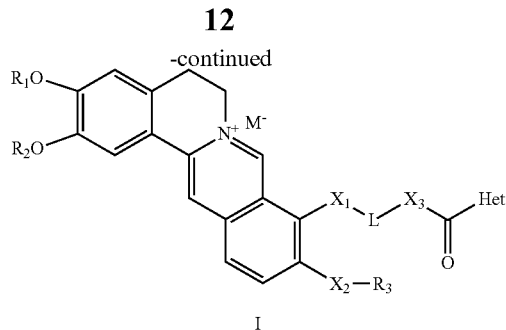

step 1: the compound of Formula IV is generated by reacting the compound of Formula II with the compound of Formula III;

step 2: the derivative of berberine of Formula I is generated by reacting the compound of Formula IV with the compound of Formula V;

wherein, $X_1$-$X_3$, $R_1$-$R_3$, L, Het, and $M^-$ are defined as set forth herein;

$T_A$ and $T_B$ independently represent a leaving group, preferably halogen, and more preferably, chlorine or bromine;

$M_1^-$ represents an anion, which is the same as or different from $M^-$. Preferably, $M_1^-$ is selected from the group comprising $F^-$, $Cl^-$, $Br^-$, $I^-$, and $CH_3COO^-$.

When the derivative of berberine of Formula I is selected from compound 1, the preparation method is as follows:

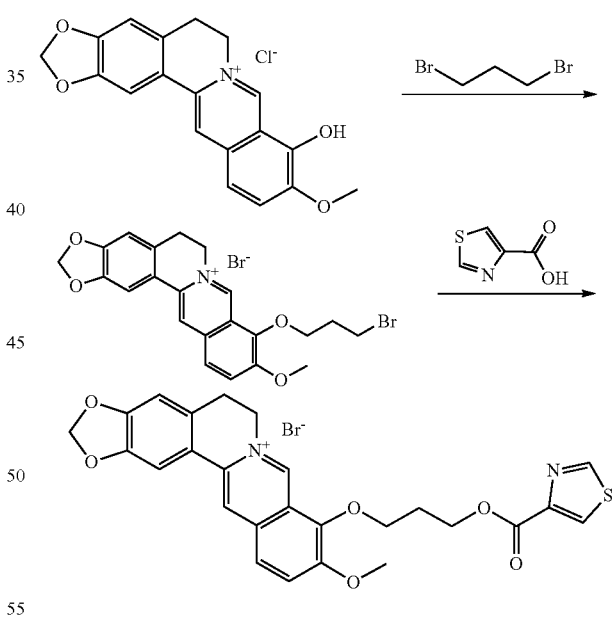

Brominated 9-O-bromopropyl berberine is obtained by reacting berberrubine with 1,3-dibromopropanol. The resulting brominated 9-O-bromopropyl berberine is subsequently reacted with thiazole-4-formate to give the final product.

The preferable examples of the present disclosure will be described in detail below. The examples illustrated herein are merely used for better understanding of the disclosure, and the scope of the disclosure is not limited to the following examples. Any immaterial improvement and modification made to the embodiments based on the disclosure still belong to the scope of the disclosure.

Example 1

Preparation of Compound 1 (brominated 9-O-propyl berberine thiazole formate)

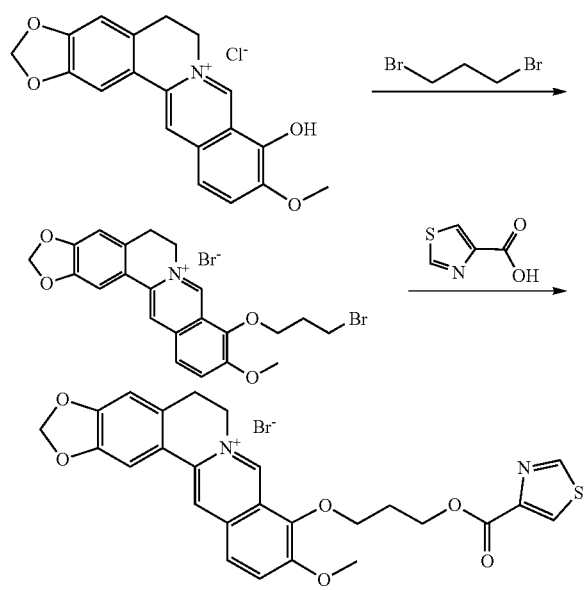

1 g berberrubine, 0.421 mg potassium carbonate, 0.93 g sodium iodide, and 15 ml DMF were sequentially added to a round-bottom flask, and heated to reflux at 80° C. for 30 min. Subsequently, 850 μl 1,3-dibromopropanol was added dropwise to the mixture which was then kept at reflux for 6 h. The reaction was monitored by TLC. After the reaction, 40 ml ethyl acetate was added, and the mixture was allowed to stand in ice water for 30 min for crystal precipitation. Then, the crude product was obtained by filtration, and dissolved in 15 ml DMF, to which 30 ml ethyl acetate was added for the second recrystallization. After suction filtration and drying, 1.31 g brominated 9-O-bromopropyl berberine was obtained with the yield of 90%. The procedure was repeated for many times to get enough amount of the intermediate.

2.019 g 9-O-bromopropyl berberine, 1.356 g thiazole-4-formic acid, 633 mg sodium iodide, 120 ml DMF and 2.33 ml triethylamine were added. After 2 hours reflux at 90° C., the reaction was stopped. After cooling, 120 ml distilled water was added to the reaction system, followed by extraction with dichloromethane (120 ml×3). The dichloromethane phases were combined, to which 480 mL petroleum ether was added, resulting in a great amount of precipitates. After suction filtration, the filter cake was collected. The product was purified by chromatography using a column wet-packed with 200 g silica gel. The elution was carried out with a gradient of $CH_2Cl_2:CH_3OH=40:1 \rightarrow 30:1$ (v/v), yielding 1.725 g yellow solid brominated 9-O-propyl berberine thiazole formate. The yield was 79%.

Figure 2:
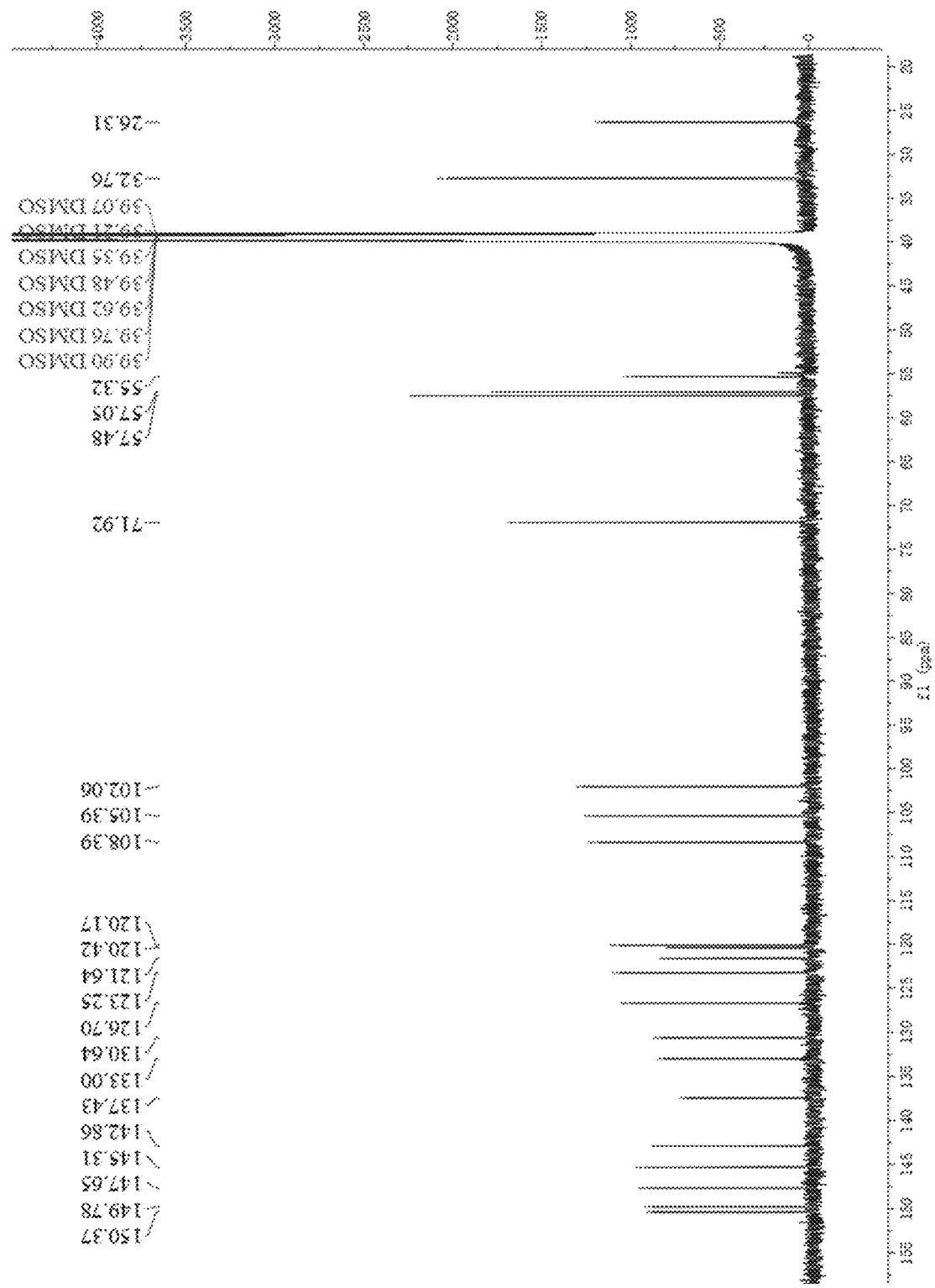
FIG. 2 illustrates the $^{13}C$ NMR spectrum of the intermediate brominated 9-O-bromopropyl berberine.

Structure Characterization of the Intermediate:

The intermediate brominated 9-O-bromopropyl berberine prepared in Example 1 was characterized for its structure. The schematic diagrams of the related signals in $^1$H NMR and $^{13}$C NMR were shown in FIG. 1 and FIG. 2.

Brominated 9-O-bromopropyl berberine, chemical name: 9-(3-bromopropoxy)-10-methoxyl-5,6-dihydro-[1,3]dioxolo[4,5-g]isoquinolyl[3,2-a]isoquinolin-7-ium bromide. It was yellow powder and dissolved in dichloromethane.

$^1$H NMR (600 MHz, DMSO-d$_6$) δ 9.82 (s, 1H), 8.97 (s, 1H), 8.21 (d, J=9.0 Hz, 1H), 8.02 (d, J=9.0 Hz, 1H), 7.80 (s, 1H), 7.10 (s, 1H), 6.18 (s, 2H), 4.97 (t, J=6.3 Hz, 2H), 4.42 (t, J=6.3 Hz, 2H), 4.07 (s, 3H), 3.84 (t, J=6.4 Hz, 2H), 3.23 (t, J=6.4 Hz, 2H), 2.43 (m, J=6.4 Hz, 2H).

$^{13}$C NMR (151 MHz, DMSO-d$_6$) δ 150.37, 149.78, 147.65, 145.31, 142.86, 137.43, 133.00, 130.64, 126.70, 123.25, 121.64, 120.42, 120.17, 108.39, 105.39, 102.06, 71.92, 57.48, 57.05, 55.32, 39.90, 39.76, 39.62, 39.48, 39.35, 39.21, 39.07, 32.76, 26.31.

Figure 3:
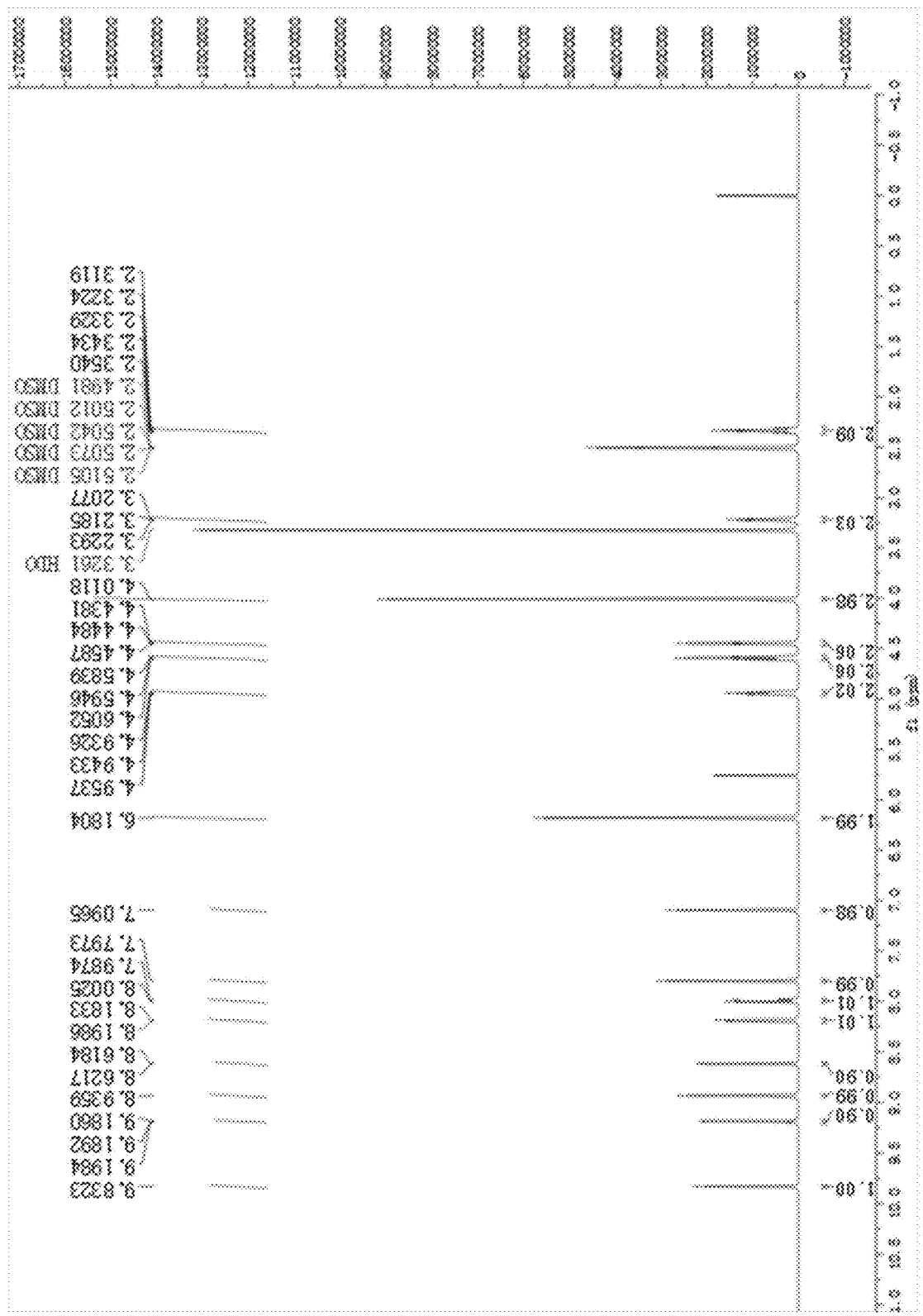
FIG. 3 illustrates the $^1H$ NMR spectrum of the brominated 9-O-propyl berberine thiazole formate.
Figure 4:
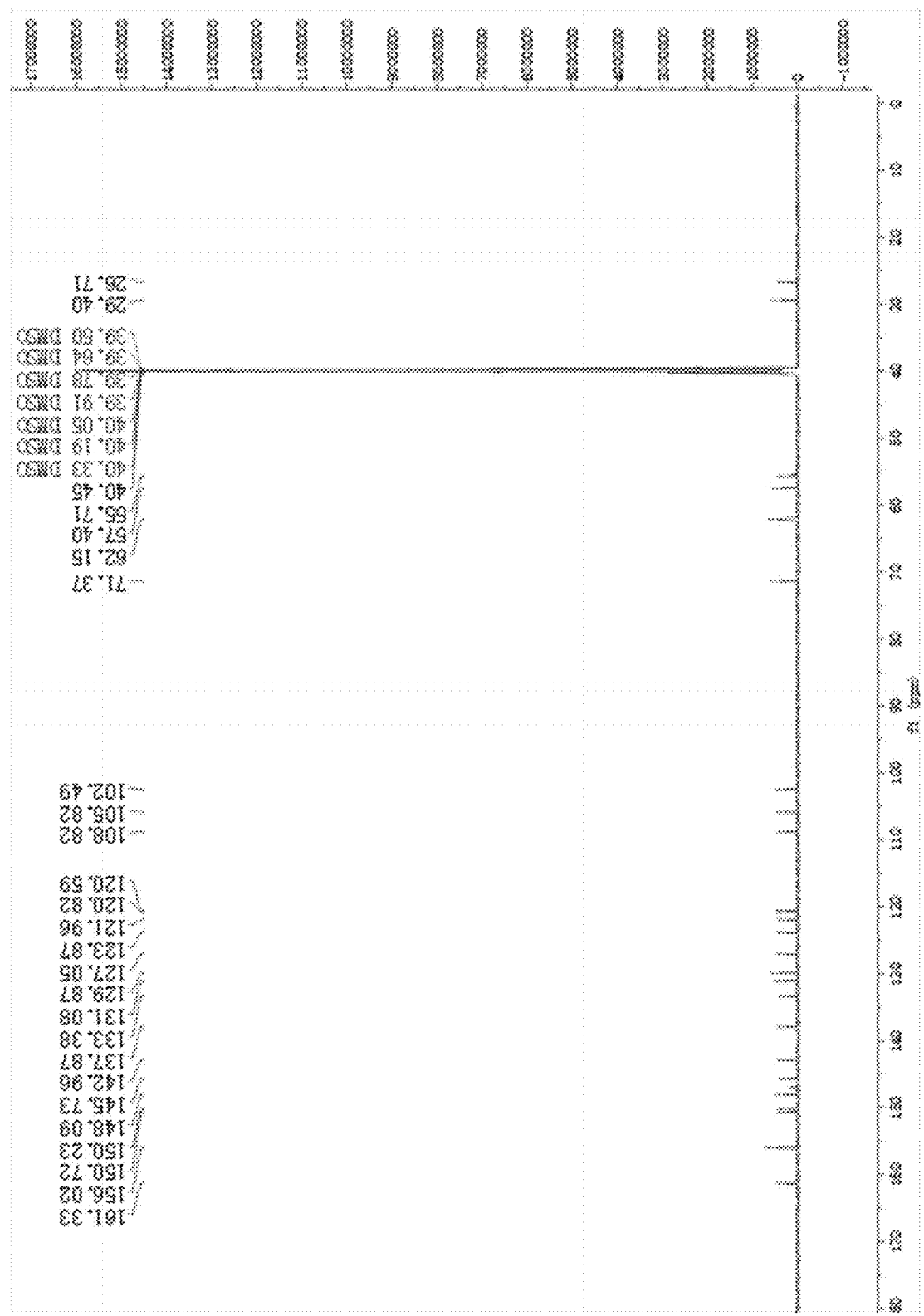
FIG. 4 illustrates the $^{13}C$ NMR spectrum of the brominated 9-O-propyl berberine thiazole formate.

Structure Characterization of the Target Compound:

The end product prepared in Example 1 was characterized for its structure. The schematic diagrams of the related signals in $^1$H NMR and $^{13}$C NMR were shown in FIG. 3 and FIG. 4.

Brominated 9-O-propyl berberine thiazole formate, chemical name: 9-(3-((thiazole-4-carbonyl)oxy)propoxy)-10-methoxy-5,6-dihydro-[1,3]dioxolo[4,5-g]isoquinolino[3,2-a]isoquinolin-7-ium bromide. It was yellow powder and dissolved in methanol.

$^1$H NMR (600 MHz, DMSO-d$_6$) δ 9.83 (s, 1H), 9.19 (d, J=1.9 Hz, 1H), 8.94 (s, 1H), 8.62 (d, J=1.9 Hz, 1H), 8.19 (d, J=9.1 Hz, 1H), 7.99 (d, J=9.1 Hz, 1H), 7.80 (s, 1H), 7.10 (s, 1H), 6.18 (s, 2H), 4.94 (t, J=6.4 Hz, 2H), 4.59 (t, J=6.4 Hz, 2H), 4.45 (t, J=6.3 Hz, 2H), 4.01 (s, 3H), 3.22 (t, J=6.3 Hz, 2H), 2.33 (m, J=6.3 Hz, 2H).

$^{13}$C NMR (151 MHz, DMSO-d$_6$) δ 161.33, 156.02, 150.72, 150.23, 148.09, 145.73, 142.96, 137.87, 133.38, 131.08, 129.87, 127.05, 123.87, 121.96, 120.82, 120.59, 108.82, 105.82, 102.49, 71.37, 62.15, 57.40, 55.71, 40.45, 29.40, 26.71.

The structure of the compound can be determined as follows based on the information described above:

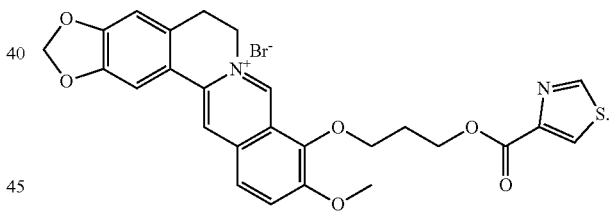

Example 2

Cytotoxicity Test on the Present Compound

1. Materials

Experiment cells: primary cardiac cells from neonatal mice

Test sample: brominated 9-O-propyl berberine thiazole formate (compound 1, prepared in Example 1)

2. Principles

The toxicity of the novel compound, brominated 9-O-propyl berberine thiazole formate, on the primary cardiac cells from neonatal mice was detected using CCK-8 assay. The CCK-8 agent contains WST-8, which has the chemical name: 2-(2-methoxy-4-nitrophenyl)-3-(4-nitrophenyl)-5-(2,4-disulfophenyl)-2H-tetrazolium sodium salt. It can be reduced to yellow formazan with high water solubility by the dehydrogenase existing in the mitochondrion in a cell in the presence of electron carrier 1-methoxy-5-methylphenazinium methyl sulfate (1-Methoxy PMS). The amount of formazan generated is proportional to the number of live cells. The absorbance is detected at a wavelength of 450 nm by an enzyme-linked immunosorbent assay, which represents the number of live cells, in which a larger value indicates a higher cell activity.

3. Experiment Methods 3.1 Culture of Primary Cardiac Cells From Neonatal Mice

Before the experiment, all equipments used in the experiment were autoclaved for 2 hour. The trypsinization solution was pre-warmed in a water-bath at 37° C. After disinfection by alcohol, the skin and sternum of the left chest were cut off at one time using a scissor. The heart was then squeezed out, taken and put into a pre-cooled FBS-free DMEM culture medium with a curved forceps. The blood vessels on the surface of heart, the residual blood and the attached lung tissue were removed. The heart tissue was cut into pieces with homogeneous size. The heart pieces were drawn into a 15 ml centrifuge tube, and the supernatant was discarded. The tissue was rinsed by PBS for 2-3 times. The trypsinization solution was added at equivalent volume of the heart tissue. The centrifuge tube was kept shaken to accelerate digestion. After the solution become turbid, the digestion was stopped by transferring the solution to DMEM culture medium. After the digestion of all heart tissues was completed, the digest was filtered by a sieve, and centrifuged at 1500 rpm for 5 min. The pellet of cells deposited at the bottom was collected by discarding the supernatant, and the DMEM culture medium containing 10% FBS was added to the centrifuge tube. The cells were pipetted to homogeneity, transferred to a bottle and incubated at 37° C. and 5% $CO_2$ for 1.5-2 hours. The culture was differentially centrifuged, and the suspended cardiac cells were aspirated and re-plated in a 96-well plate. The plate was cultured for another 48 hours, and the cells in a good condition were used for further experiments.

3.2 Administration of the Compound and CCK-8

After digestion, the primary cardiac cells from neonatal mice were re-suspended into a 96-well plate at a appropriate concentration with volume of 100 μl for each well. After culturing for another 48 hours, the medium was changed under a good condition by adding 0.1, 0.5, 1, 5, 10, 50, 100, 500, and 1000 μM brominated 9-O-propyl berberine thiazole formate. For each concentration, 5 wells were repeated for culturing for 24 hours. 24 hours later, CCK-8 solution was diluted by DMEM culture medium in a ratio of 1:10 in dark. The medium was changed. After incubation at 37° C. for 1-4 hours, the mixture was placed in a micro-plate reader and shaken for 10 s. The absorbance at 450 nm ($OD_{450}$) was recorded.

4. Experiment Data and Results 4.1 Data Processing

The relative inhibition rate of the compound at various concentrations on the primary cardiac cells from neonatal mice was calculated based on the equation: cell inhibition rate (%)=(1−$OD_{450}$ of the sample group/$OD_{450}$ of the control group)*100. Subsequently, the $IC_{50}$ value of the compound was calculated by dose-effect curve fitting. The Experiment data were expressed as mean±standard error. The $OD_{450}$ value for each group was analyzed by One-way ANOVA, with P<0.05 indicating a significant difference. All experiment results were statistically analyzed and plotted using Graphpad Prism 8.0.

4.2 Experiment Results

Figure 5A:
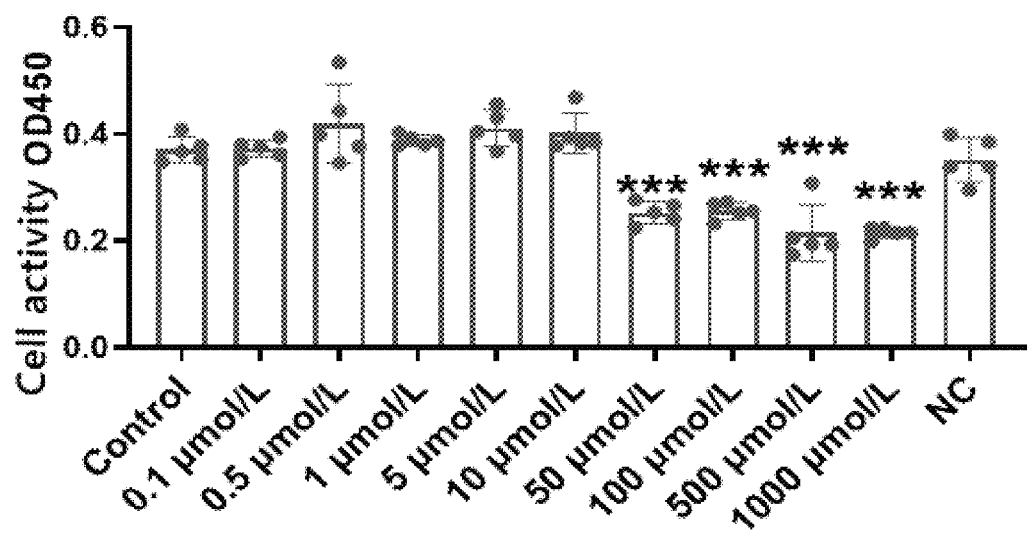
FIGS. 5A-B illustrate the cytotoxicity of the brominated 9-O-propyl berberine thiazole formate.
Figure 5B:
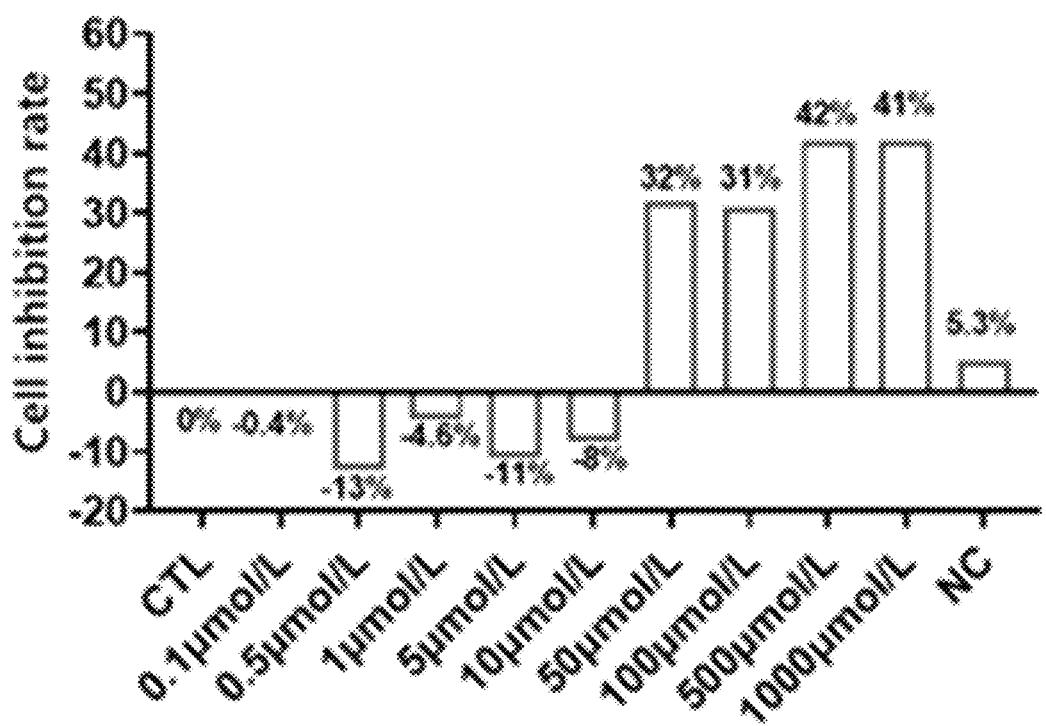

The toxicity of brominated 9-O-propyl berberine thiazole formate was shown in FIGS. 5A-5B. The cell inhibition rate was only 41% for the compound brominated 9-O-propyl berberine thiazole formate at the concentration of 1000 μM. As indicated by the experiment above, the compound brominated 9-O-propyl berberine thiazole formate had low toxicity at the concentration range tested.

Example 3

Efficacy Test 1 of the Present Compound

1. Materials

Experiment animals: 25 C57BL/6 male mice with body weight ranging from 25 to 30 g The test compound: brominated 9-O-propyl berberine thiazole formate (Compound 1, prepared in Example 1), the control compound: berberine, and the positive control: sacubitril and valsartan sodium.

2. Principles

The mouse model of myocardial infarction was established by ligation of the left anterior descending branch of the coronary artery. The agent was then administrated to the mice to determine the effect of the test sample on myocardial ischemia, and the effect of the test sample on the cardiac functions of the myocardial infarct mice.

3. Experiment Methods 3.1 Animal grouping

Random grouping: the C57BL/6 mice were randomly divided into 5 groups, namely the sham-operation group, the myocardial infarction group, the berberine group (berberine at a dosage of 40 mg/kg·$d^{-1}$), the test compound group (brominated 9-O-propyl berberine thiazole formate at a dosage of 40 mg/kg·$d^{-1}$) and the positive control group (sacubitril and valsartan sodium at a dosage of 26 mg/kg·$d^{-1}$).

3.2 Establishment of the Myocardial Infarction Model

The mouse model of myocardial ischemia was established by ligation of the left anterior descending branch of the coronary artery. Healthy male C57BL/6 mice (28±2 g) were anesthetized by intraperitoneal injection of aphrodin (0.2 g/kg). The anesthetic mice were placed in a supine position on the operation desk with the trachea connected to a ventilator by inserting a tracheal tube. An incision of about 0.5~4.0 cm was made on the skin of the left chest from the upper left to the lower right. Pectoralis minor and serratus anterior were separated. The intercostal muscle was bluntly separated between the fourth and fifth rib, and the heart was slightly squeezed out. The coronary artery was ligated by a 7/0 ligature at the descending anterior branch of the left coronary artery 1~2 mm from the inferior margin of the left atrium. After ligation, the apex of heart was observed to become pale, and S-T segment elevation was apparent in the cardiogram.

3.3 Administration and Modeling Period

Except for the sham-operation group, coronary artery ligation was performed to all other mice. The mice were randomly divided into 4 groups 24 hours after ligation, including the myocardial infarction group, the berberine group, the brominated 9-O-propyl berberine thiazole formate group and the positive control group. Blank solvent, berberine, brominated 9-O-propyl berberine thiazole formate and positive control sacubitril and valsartan sodium were administrated to the mice by gavage (as shown in Table 1) for consecutive 14 days. Subsequently, ultrasonography was performed to determine the cardiac function of the mice in each group.

TABLE 1

Administration and diet for the animals in each group.

| Groups | Frequency of administration | Administration cycle | Dosage | Agent for administration | Number of mice |
| --- | --- | --- | --- | --- | --- |
| Sham-operation group | Gavage once per day | 2 weeks | 5 ml/kg body weight | Solvent | 5 |
| Myocardial infarction group | Gavage once per day | 2 weeks | 5 ml/kg body weight | Solvent | 5 |
| Berberine group | Gavage once per day | 2 weeks | 40 mg/kg body weight | Berberine | 5 |
| Brominated 9-O-propyl berberine thiazole formate group | Gavage once per day | 2 weeks | 40 mg/kg body weight | Brominated 9-O-propyl berberine thiazole formate | 5 |
| Positive control group | Gavage once per day | 2 weeks | 26 mg/kg body weight | Sacubitril and valsartan sodium | 5 |

3.4 Observation Period

General vital signs were observed during experimentation.

3.5 Principal Detection Indices

Ultrasonography was performed 2 weeks after gavage to determine the cardiac functions.

4. Experiment Data and Results 4.1 Data Processing

The Experiment data were expressed as mean±standard error. One-way ANOVA was employed for multi-group comparison, and T test was used for comparison between two groups. P<0.05 indicated a significant difference. All experiment results were statistically analyzed by Graphpad Prism 8.0.

4.2 Experiment Results

Figure 6A:
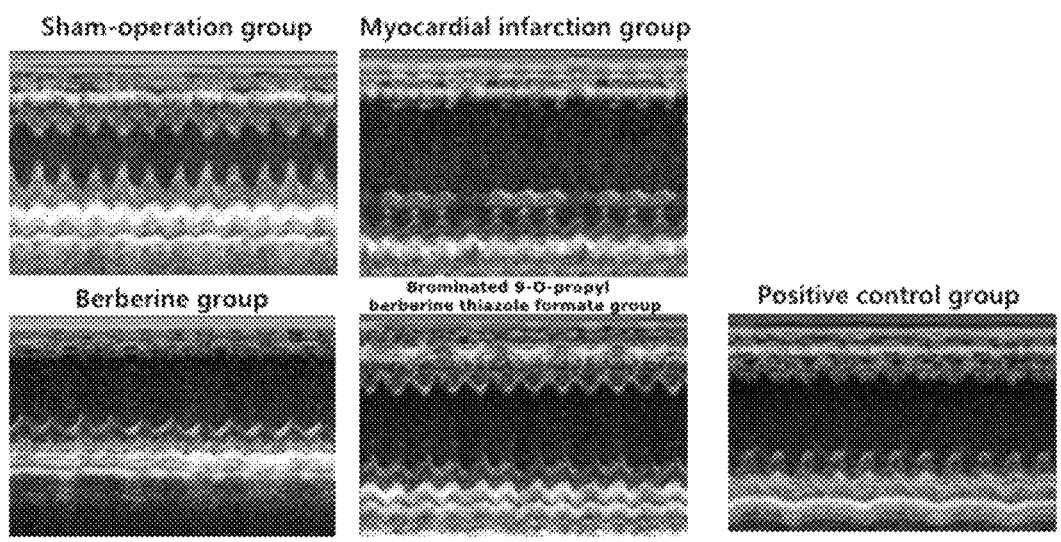
FIGS. 6A-6C illustrate the effect of the brominated 9-O-propyl berberine thiazole formate on the cardiac function of the myocardial infarcted mice.
Figure 6B:
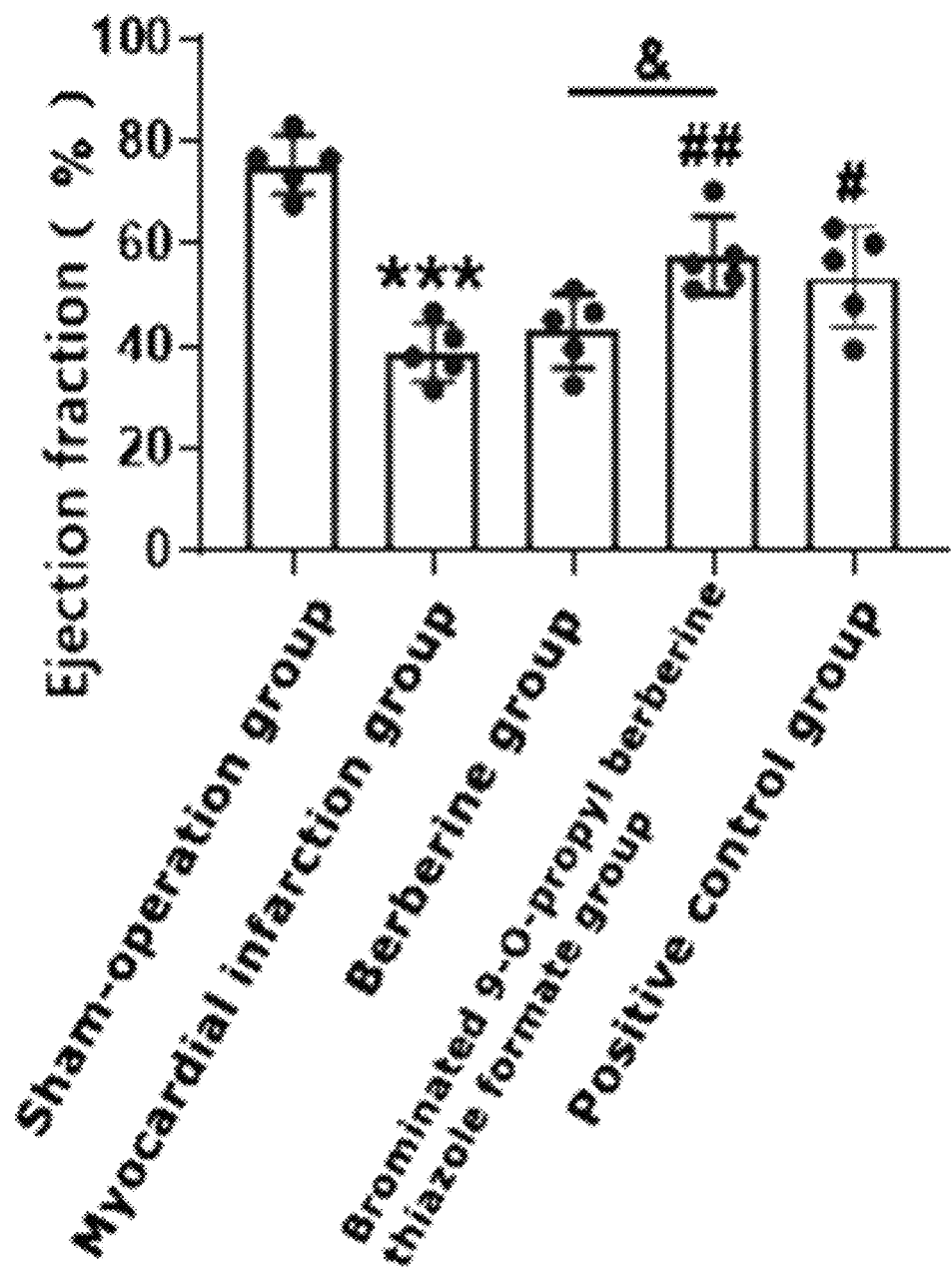
Figure 6C:
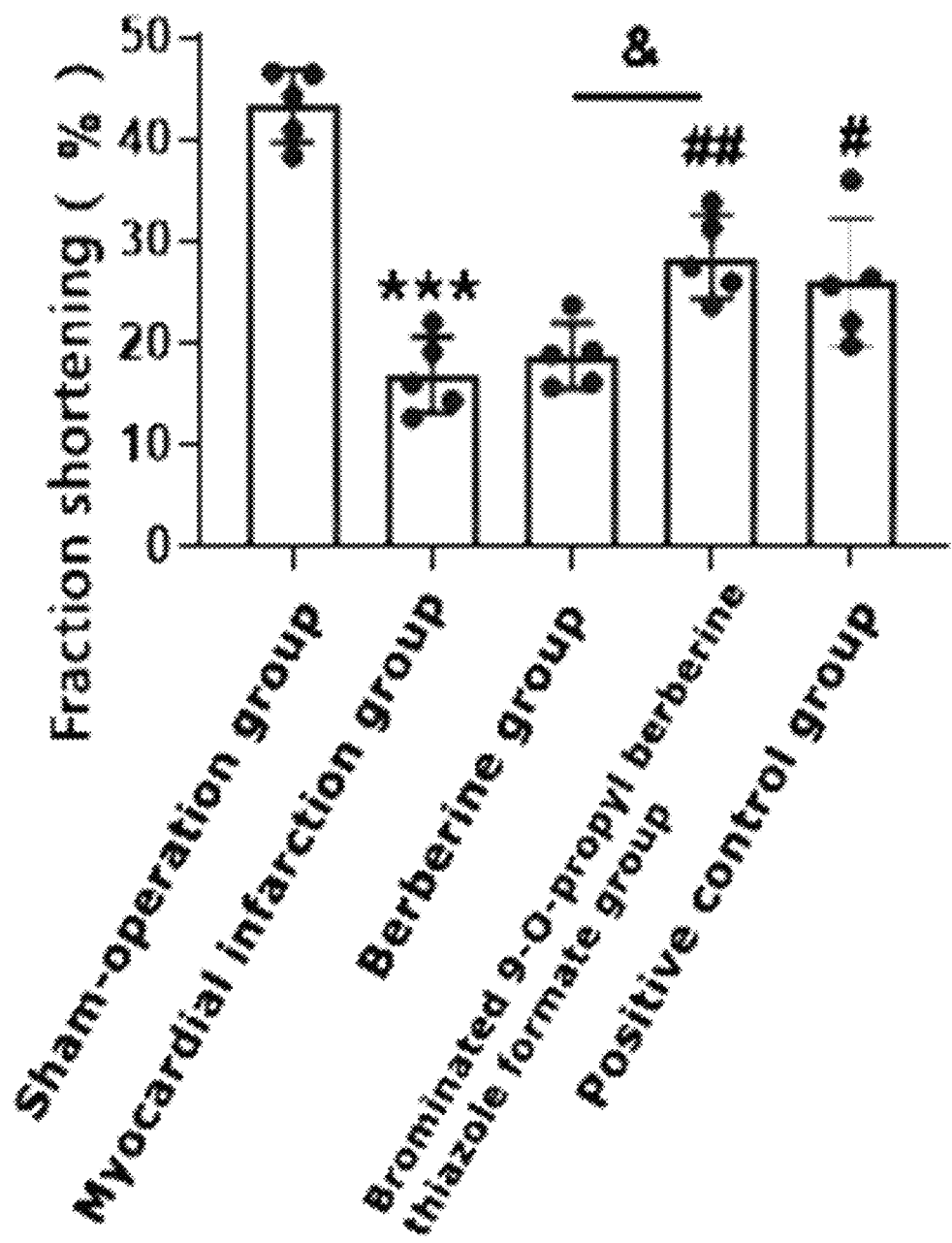

The mouse model of myocardial infarction was established by ligation of the left anterior descending branch of the coronary artery, as shown in FIGS. 6A-6C (data were expressed as mean±standard deviation, with *P<0.001 vs. the sham-operation group, #P<0.05, ##P<0.01 vs. the myocardial infarction group. For the sham-operation group, n=5; for the myocardial infarction group, n=5; for the brominated 9-O-propyl berberine thiazole formate group (40 mg/kg), n=5; for the berberine group (40 mg/kg), n=5). Two weeks after the ligation of the left anterior descending branch of the coronary artery of the mice, the ejection fraction (EF) and fraction shortening (FS) of the mice in the myocardial infarction group were significantly decreased as compared to the sham-operation group (*P<0.001 vs. the sham-operation group). However, in the brominated 9-O-propyl berberine thiazole formate group, both EF and FS were significantly increased in comparison with the myocardial infarction group (##P<0.01 vs. the myocardial infarction group) with a statistically significant difference. The effect of the brominated 9-O-propyl berberine thiazole formate was also better than that of the berberine (&P<0.05 vs. the berberine group). The results indicated that the brominated 9-O-propyl berberine thiazole formate could alleviate the injuries caused by myocardial ischemia in mice, and outperformed berberine.

Example 4

Efficacy Test 2 of the Present Compound

This Example showed the protection effect of the brominated 9-O-propyl berberine thiazole formate on the injuries caused by $H_2O_2$ in the primary cardiac cells from neonatal mice.

1. Materials

Experiment cells: primary cardiac cells from neonatal mice

Test sample: brominated 9-O-propyl berberine thiazole formate (compound 1, prepared in Example 1), and the control compound: berberine.

2. Principles 2.1 The Principle for SOD Assay

Dismutation of superoxide anion can be catalyzed by superoxide dismutase (SOD) to give hydrogen peroxide and oxygen. SOD is a kind of important antioxidases in organisms. SOD plays a vital role in the equilibrium between oxidation and anti-oxidation in organisms. SOD is able to scavenge superoxide anion free radicals and protect cells from injuries. In this test, the SOD activity was determined using WST-1 assay.

2.2 The Principle for ATP Detection

A kit has been used in this study, based on that ATP is demanded to provide energy during the fluorescence production by the fluorescein catalyzed by the firefly luciferase (also termed as luciferase). When both luciferase and fluorescein are excessive, in a certain concentration range, the fluorescence generated is proportional to the concentration of ATP. That is, the concentration of ATP in the solution can be detected sensitively.

3. Experiment Methods 3.1 Culture of Primary Cardiac Cells From Neonatal Mice

After disinfecting the neonatal mice (within 3 days after birth) by alcohol, the skin and sternum of the left chest were cut off at one time using a scissor. The heart was then squeezed out, taken and put into a pre-cooled FBS-free DMEM culture medium with a curved forceps. The blood vessels on the surface of heart, the residual blood and the attached lung tissue were removed. The heart tissue was cut into pieces with homogeneous size. The heart pieces were drawn into a 15 ml centrifuge tube, and the supernatant was discarded. The tissue was rinsed by PBS for 2-3 times. The trypsinization solution was added at equivalent volume of the heart tissue. The centrifuge tube was kept shaken to accelerate digestion. After the solution become turbid, the digestion was stopped by transferring the solution to DMEM culture medium. After the digestion of all heart tissues was completed, the digest was filtered by a sieve, and centrifuged at 1500 rpm for 5 min. The pellet of cells deposited at the bottom was collected by discarding the supernatant, and the DMEM culture medium containing 10% FBS was added to the centrifuge tube. The cells were pipetted to homogeneity, transferred to a bottle and incubated at 37° C. and 5% $CO_2$ for 1.5-2 hours. The culture was differentially centrifuged, and the suspended cardiac cells were aspirated and re-plated in a 6-well plate. The plate was cultured for another 48 hours, and the cells in a good condition was used for further experiments.

3.2 Administration and Detection

After digestion, the primary cardiac cells from neonatal mice were re-suspended into a 6-well plate at a appropriate concentration with volume of 2 mL for each well. After culturing for another 48 hours, the medium was changed under a good condition. Cell injury was induced by $H_2O_2$ (100 μM) for 12 hours to simulate the ischemic injury of cardiac cells. The brominated 9-O-propyl berberine thiazole formate was added at a final concentration of 1, 2.5, and 5 μM, with 5 μM berberine as the control. For each concentration, 4 wells were repeated for culturing for 24 hours. The primary cardiac cells from neonatal mice were collected, rinsed by PBS, digested by trypsin, and finally collected in a PBS buffer. The mixture was centrifuged at 4° C. and 1000 rpm for 10 min. The supernatant was discarded. The activity of SOD and the content of ATP in the cells were determined according to the instruction provided in the SOD and ATP detection kit, respectively. All experiments were carried out in triplicate.

4. Experiment Data and Results 4.1 Data Processing

The experiment data were expressed as mean±standard error. The SOD and ATP content in the cells in each group were analyzed by One-way ANOVA, with $P<0.05$ indicating a significant difference. All experiment results were statistically analyzed and plotted using Graphpad Prism 8.0.

4.2 Experiment Results (1) Change of the SOD Content in the Primary Cardiac Cells From Neonatal Mice As compared with the model group, the SOD content increased in the primary cardiac cells from neonatal mice in the brominated 9-O-propyl berberine thiazole formate group (1, 2.5, and 5 μM) (#$P<0.05$, ###$P<0.001$), in which the highest enhancement of the SOD content was 43.4% in the cardiac cells, apparently better than the effect of berberine at the same concentration (&$P<0.05$). The experiment results were shown in FIG. 7 (the bars in the figure, from left to right, represented the concentration of 1.0 μM, 2.5 μM, and 5.0 μM, respectively).

(2) Change of the ATP Content in the Primary Cardiac Cells From Neonatal Mice

As compared with the model group, the ATP content increased in the primary cardiac cells from neonatal mice in the brominated 9-O-propyl berberine thiazole formate group (1, 2.5, and 5 μM) (##$P<0.01$, ###$P<0.001$), in which the highest enhancement of the ATP content was 59.1% in the cardiac cells, apparently better than the effect of berberine at the same concentration (&&$P<0.01$). The experiment results were shown in FIG. 8.

Figure 7:
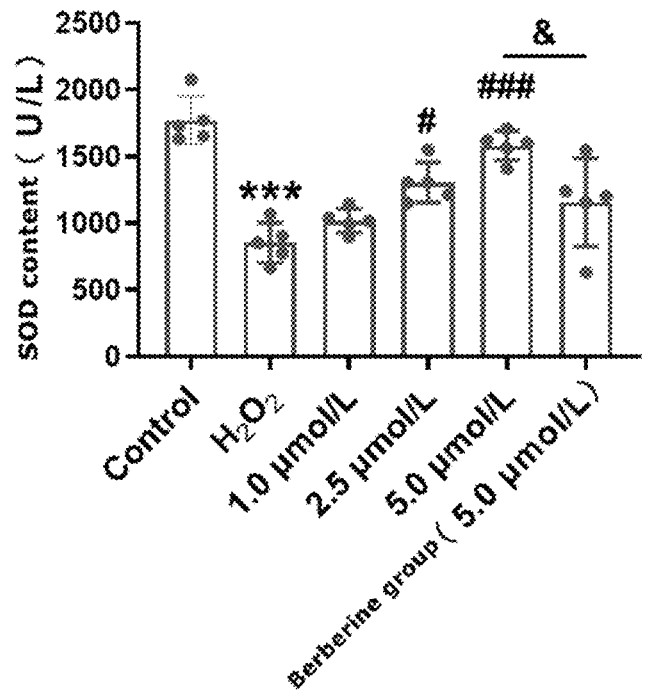
FIG. 7 illustrates the effect of the brominated 9-O-propyl berberine thiazole formate on SOD in the primary cardiac cells from neonatal mice after $H_2O_2$ treatment.
Figure 8:
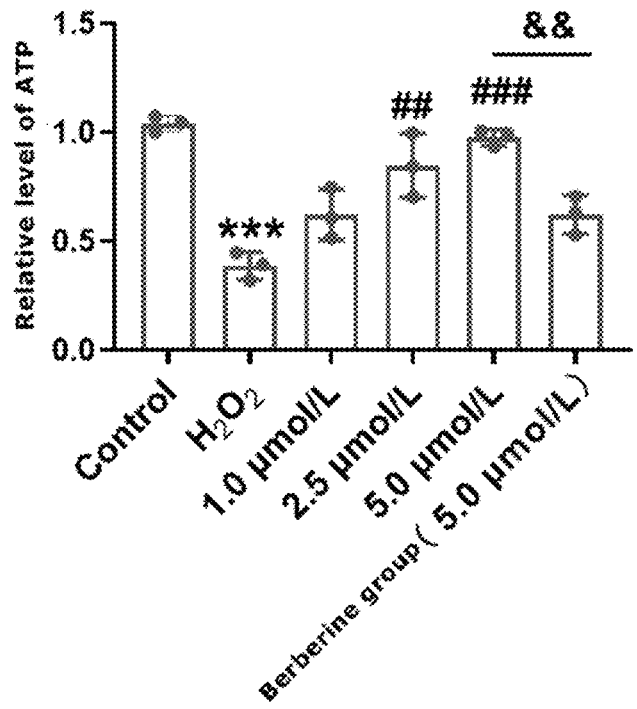
FIG. 8 illustrates the effect of the brominated 9-O-propyl berberine thiazole formate on ATP in the primary cardiac cells from neonatal mice after $H_2O_2$ treatment.

It should be noted that, in FIG. 7 and FIG. 8, * represents the relative value as compared with the control group, in which *** represents $P<0.001$; and # represents the relative value as compared with the model group, in which # represents $P<0.05$, ## represents $P<0.01$, and ### represents $P<0.001$; and & represents the relative value as compared with both ends of the line, in which & represents $P<0.05$, and && represents $P<0.01$.

Finally, it should be explained that the above preferable examples are used only for explaining the technical proposals of the present disclosure, and are not limited thereto. Although the present disclosure has been described in detail with reference to the above preferable examples, it should be understood that by those skilled in the art that various changes in format and details may be made without departing from the scope limited by the claims of the disclosure.

The invention claimed is:

1. A compound of Formula I, or the pharmaceutically acceptable salts, stereoisomers, polymorphisms, solvates and hydrates thereof:

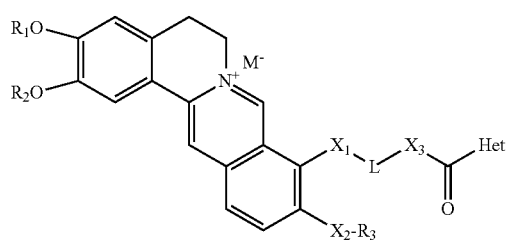

wherein, $X_1$, $X_2$, and $X_3$ are —O—;

$R_1$ and $R_2$ form together —$CH_2$—;

$R_3$ is $C_{1-6}$ alkyl;

L is —$(CHR_L)_m$—, wherein $R_L$ is hydrogen, and m is selected from 1, 2, 3, 4, 5 or 6;

Het is selected from the group consisting of oxazolyl, thiazolyl, imidazolyl, pyrazolyl, isoxazolyl, isothiazolyl, which is optionally substituted by one or more of the substituents selected from the group consisting of methyl, ethyl, n-propyl, isopropyl;

$M^-$ represents an anion.

2. The compound of Formula I or the pharmaceutically acceptable salts, stereoisomers, polymorphisms, solvates and hydrates thereof according to claim 1, wherein Het is thiazyl.

3. The compound of Formula I or the pharmaceutically acceptable salts, stereoisomers, polymorphisms, solvates and hydrates thereof according to claim 1, wherein the compound of Formula I is selected from the group consisting of:

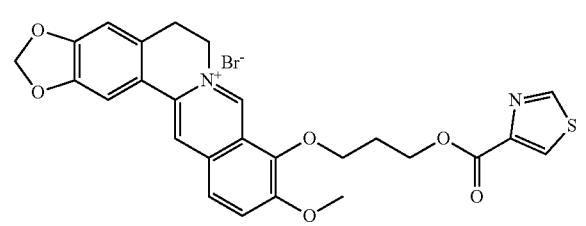

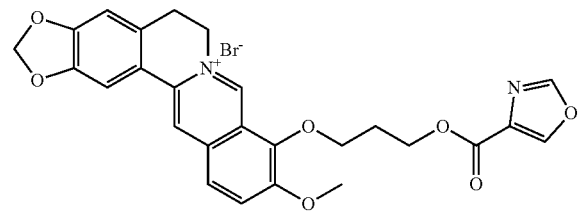

-continued
3
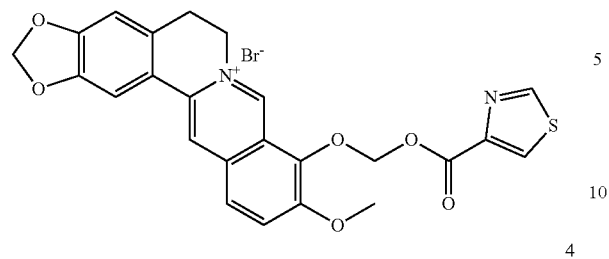
4
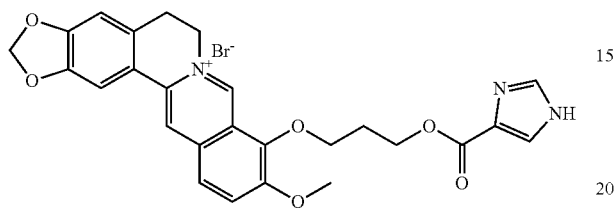
5
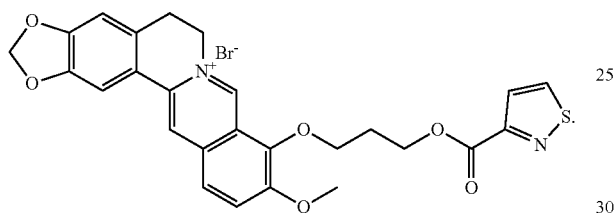
* * * * *